United States Patent
Chaudhari et al.

(10) Patent No.: US 7,189,882 B2
(45) Date of Patent: Mar. 13, 2007

(54) SELECTIVE LIQUID PHASE OXIDATION OF TOLUENE TO BENZALDEHYDE

(75) Inventors: Raghunath Vittal Chaudhari, Pune (IN); Vilas Hari Rane, Pune (IN); Amit Arwind Deshmukh, Pune (IN); Sunil Sadashiv Divekar, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/317,750

(22) Filed: Dec. 23, 2005

(65) Prior Publication Data

US 2006/0135820 A1 Jun. 22, 2006

Related U.S. Application Data

(63) Continuation of application No. 10/810,339, filed on Mar. 26, 2004, now abandoned.

(51) Int. Cl.
*C07C 45/36* (2006.01)

(52) U.S. Cl. ..................................... 568/431; 568/437
(58) Field of Classification Search .................... None
See application file for complete search history.

(56) References Cited

U.S. PATENT DOCUMENTS 6,495,726 B1 * 12/2002 Kantam et al. ............. 568/431

OTHER PUBLICATIONS

Borgaonkar et al. Liquid Phase Oxidation of Toluene to Benzaldehyde by Air. Industrial Engineering and Chemical Product Research and Development, 1984, vol. 23, p. 455-458.*

* cited by examiner

*Primary Examiner*—Sikarl A. Witherspoon
(74) *Attorney, Agent, or Firm*—Darby & Darby

(57) ABSTRACT

The present invention provides an improved process for the liquid phase oxidation of toluene to benzaldehyde with high selectivity and good activity in an organic acid medium using a catalyst system consisting of transition metal/metals and bromide as a promoter in the presence of lean oxygen.

28 Claims, No Drawings

SELECTIVE LIQUID PHASE OXIDATION OF TOLUENE TO BENZALDEHYDE

CROSS-REFERENCE OF RELATED APPLICATIONS

This application is a continuation of U.S. patent application Ser. No. 10/810,339, filed Mar. 26, 2004 now abandoned.

FIELD OF THE INVENTION

The present invention provides an improved process for the liquid phase oxidation of toluene to benzaldehyde with high selectivity and good activity in an organic acid medium using a catalyst system consisting of transition metal/metals and bromide as a promoter in the presence of lean oxygen.

BACKGROUND OF THE INVENTION

Benzaldehyde is widely used as an intermediate in the manufacture of dyestuff, flavoring chemicals (e.g. cinnamldehyde, amyl cinnamldehyde and benzyl benzoate), perfumery chemicals, in acriline dyes, pharmaceuticals and fine chemicals. It can be also used as a corrosion inhibitor and a solvent for polyester resins.

Benzaldehyde is produced by the hydrolysis of the corresponding side chain halogenated toluene compounds such as benzyl chloride at a temperature range of 100°–200° C. at normal or higher pressures in the presence of an excess hydrochloric acid (U.S. Pat. No. 4,229,379). In U.S. Pat. No. 4,450,298 a process is described for the vapor phase catalytic hydrolysis of benzyl chloride to benzaldehyde using a catalyst comprising activated carbon treated with sulphuric acid or impregnated with a metal chloride such as iron (III) chloride or a metal sulphate such as cupric sulphate. A major disadvantage of these processes is the generation of large amount of effluent. The benzaldehyde produced by these routes does not meet food grade specifications.

Vapor phase or liquid phase oxidation of toluene by air or $O_2$ is environmentally benign and provided the desired selectivities to the market driven products. World patent WO 95/20560 discloses a liquid phase process for the manufacture of benzaldehyde by the oxidation of toluene in presence of oxygen in a temperature and pressure range of 120°–200° C. and 2–50 atm, respectively in the presence of a catalyst comprising cobalt or manganese as a metal ion and bromide as a promoter. 10% conversion of toluene and 45% selectivity to benzaldehyde is obtained. Borgaonkar et al, [I & EC Prod. Res. Dev., 23(3), 459 (1984)] have reported lower (10%) conversion of toluene and 90% yield of benzaldehyde by the use of cobalt acetate and either sodium bromide or paraldehyde as a promoter in presence of air.

A process for the vapor phase oxidation of toluene to benzaldehyde and benzoic acid using a catalyst containing a mixture of silver vanadate and lead vanadate or silver arsenate in presence of oxygen or ozone is described in U.S. Pat. No. 3,485,876. This catalyst system suppresses the formation of benzoic acid and degradation to carbon dioxide. According to U.S. Pat. No. 3,946,067, aromatic aldehydes such as benzaldehyde or substituted benzaldehydes were manufactured by the vapour-phase oxidation of aralkyl compounds, like toluene or substituted toluenes, in the presence of catalyst containing palladium metal and phosphoric acid at a temperature of less than 250° C. The aromatic aldehydes are produced in a single reaction step. The drawbacks of the process are that the conversion of toluene has to be kept very low (<4%) for obtaining high selectivity (>70%). Also, the process is not suitable as large amounts of carbon dioxide are formed due to high temperature used in the reaction. U.S. Pat. No. 4,390,728 describes a process in which the oxides of various metals (viz. Cu, Fe, Pb, Mo, U, and P) with promoter were used for the production of benzaldehyde by the oxidation of toluene. At a temperature of 475–550° C., a conversion of 35–50% and selectivity of 40–70% to benzaldehyde was obtained. U.S. Pat. No. 4,137,259 describes a process wherein silver vanadate and iron vanadate on silica is used as a catalyst at a temperature range 300°–500° C. in the presence of oxygen or ozone and steam. The conversion of toluene was found to be 21% and lower selectivity to aldehyde. A large amount of carbon oxide formation was observed in this process. U.S. Pat. No. 3,989,674, describes a process using Cu—Au silica catalyst system. In this process, a mixture of toluene, oxygen and helium in the molar ratio of 1:2:8 is passed over the catalyst at atmospheric pressure and temperature in the range of 230–390° C. The selectivity to benzaldehyde of 75–80% was obtained at a conversion level of only 15–30%. Another process for the production of benzaldehyde was reported by Ray et al. [Ind. J. Technol., 21(4), 137 (1983)] at a conversion of about 15% and selectivity of 70% with significant amount of $CO_2$ formation. Hence, the major disadvantages of the above processes are the use of high temperatures and lower conversion of toluene. The formation of large amount of carbon dioxide ultimately will affect the overall yield and is also not environmentally clean. Thus, because of the above drawbacks these processes are not promising for the production of benzaldehyde by toluene oxidation.

Parteinheimer (J. Mol. Catal. 67, 35, 1991) has reported the use of HBr as a promoter in the cobalt catalyst system for the liquid phase oxidation of toluene. For this catalyst system, a very low yield for benzaldehyde (3%) and high yield of benzoic acid (91%) was obtained. Recently, in U.S. Pat. No. 6,495,726 a process is described for the production of benzaldehyde by liquid phase air oxidation of toluene using cobalt and manganese metal salts in the presence of zinc bromide as a promoter. The selectivity to benzaldehyde was reported to be 63% with toluene conversion of only 13%.

OBJECTS OF THE INVENTION

The main objective of the present invention is to provide an improved process for the manufacture of benzaldehyde by the liquid phase oxidation of toluene using a catalyst consisting of transition metal/metals and bromide as a promoter, preferably with 60–75% selectivity and good activity Yet another object of the present invention is to develop a process, which will be eco-friendly and avoids the effluent disposal problem.

Yet another object of this investigation is to explore a new catalyst system consisting of transition group metal such as manganese, chromium, iron, vanadium, cobalt, molybdenum or a combination of any of the above two metals, preferably manganese-iron or manganese-vanadium promoted with bromide.

Another object of this invention is to use a very low concentration of oxygen (5%, balance $N_2$) to achieve high selectivity to benzaldehyde.

Yet another object of this invention is to reduce the formation of side products such as benzyl alcohol and benzoic acid.

Another object of the invention is to eliminate the formation of carbon dioxide.

SUMMARY OF THE INVENTION

Accordingly the present invention provides a process for the preparation of benzaldehyde comprising subjecting toluene to liquid phase oxidation in an organic solvent and in the presence of a catalyst system comprising of transition metal/metals and a bromide source as a promoter and in the presence of diluted oxygen, cooling the reaction mixture to room temperature and separating the product.

In another embodiment of the invention, the product is separated by distillation.

In another embodiment of the invention, the transition metal is selected from the group consisting of manganese, chromium, iron, vanadium, cobalt, molybdenum, and any combination thereof, preferably, a combination of manganese and iron or manganese and vanadium.

In yet another embodiment of the invention, the mole ratio manganese to iron or manganese to vanadium is in the range of 0.1 to 10 and preferably in the range of 0.2 to 5.0.

In another embodiment of the invention, the transition metal is used in the form of a salt selected from the group consisting of acetates, bromides, carbonates, fluoride, iodides, chlorides, nitrates, sulfates and vanadates preferably acetates, chlorides and vanadates.

In yet another embodiment of the invention, the bromide promoter is selected from the group consisting of sodium bromide, hydrogen bromide and zinc bromide, preferably sodium bromide.

In another embodiment of the invention, the concentration of manganese with respect to toluene is in the range of 0.1–7 mol %, preferably 0.3–5.0 mol %.

In another embodiment of the invention, the concentration of iron or vanadium with respect to toluene is in the range of 0.1–5 mol %, preferably 0.3–4.0 mol %.

In another embodiment of the invention, the concentration of the bromine with respect to toluene is in the range of 0.05–5.0 mol %, preferably 0.1 to 3.0 mol %.

In another embodiment of the invention, the organic solvent comprises an aliphatic acid or an aromatic organic acids.

In another embodiment of the invention, the organic solvent is selected from the group consisting of acetic acid, benzoic acid and propionic acid, preferably acetic acid.

In another embodiment of the invention, the concentration of oxygen is in the range of 1–10%, preferably 2–7% in nitrogen.

In another embodiment of the invention, the reaction is carried out at a temperature and pressure preferably are in the range of 70°–180° C. and 1–80 bar, more preferably 90°–160° C. and 20–70 bar, respectively.

In another embodiment of the invention, the selectivity to benzaldehyde obtained preferably in the range of 60–75% along with benzoic acid and benzyl alcohol as side products.

DETAILED DESCRIPTION OF THE INVENTION

The present invention provides an improved process for the manufacture of benzaldehyde by liquid phase oxidation of toluene with a catalyst system consisting of transition group metal/metals such as manganese, chromium, iron, vanadium, cobalt, molybdenum or a combination of any of the above two metals, preferably manganese-iron or manganese-vanadium and bromide source as a promoter in an organic solvent in presence of dilute oxygen.

The reactions are carried out at a temperature ranging between 70°–180° C. and pressure of 5% $O_2$ (balance $N_2$) of 1–80 bar, in a stirred reactor for a period of 1–6 h. After the reaction is complete, the reaction mixture is cooled to room temperature. The reactants and products were analyzed by GC and HPLC. The products were identified by gas chromatograph—mass spectroscopy (GCMS). The present invention produces benzaldehyde with high selectivity (preferably 60–75%) along with other byproducts such as benzyl alcohol and benzoic acid. The bimetallic catalyst system is necessary for obtaining high selectivity to benzaldehyde. Individual metals such as manganese, iron or vanadium alone, lead to very low selectivity to benzaldehyde.

The process of the present invention comprises subjecting toluene to liquid phase oxidation in an organic solvent and in the presence of a catalyst system comprising of transition metal/metals and a bromide source as a promoter. The reaction is carried out in the presence of diluted oxygen and at a temperature in the range of 70°–180° C. and pressure range of 1–80 bar for a period of 1–6 h. After the reaction is complete, the reaction mixture is cooled to room temperature and the products separated by any conventional method such as distillation. The catalyst consists of transition group metal selected from manganese, chromium, iron, vanadium, cobalt, molybdenum, or a combination of any of the above two metals, preferably manganese-iron or manganese-vanadium with bromide as a promoter. The mole ratio of manganese to iron or manganese to vanadium is used in the range of 0.1 to 10 and preferably in the range of 0.2 to 5.0. The transition metal can also be taken in the form of a salt selected from acetates, bromides, carbonates, fluoride, iodides, chlorides, nitrates, sulfates, vanadates preferably acetates, chlorides or vanadates.

The bromide promoter can be selected from sodium bromide, hydrogen bromide or zinc bromide, preferably sodium bromide. The concentration of manganese with respect to toluene is in the range of 0.1–7 mol %, preferably 0.3–5.0 mol %. The concentration of iron or vanadium with respect to toluene is in the range of 0.1–5 mol %, preferably 0.3–4.0 mol %. The concentration of the bromine with respect to toluene used is in the range of 0.05–5.0 mol %, preferably 0.1 to 3.0 mol %. The organic solvent used for the reaction is selected from aliphatic and aromatic organic acids like acetic acid, benzoic acid, propionic acid, preferably acetic acid. The concentration of oxygen used as an oxidant is in the range of 1–10%, preferably 2–7% in nitrogen.

The reaction is carried out at a temperature and pressure preferably are in the range of 70°–180° C. and 1–80 bar, more preferably 90°–160° C. and 20–70 bar, respective selectivity to benzaldehyde obtained preferably in the range of 60–75% along with benzoic acid and benzyl alcohol as side products.

The process of the invention is described in detail in the following illustrative but non-limitative examples.

EXAMPLE 1

This example illustrates the reaction procedure for the liquid phase oxidation process. The reaction was carried out in a stirred reactor of 300 ml capacity having a temperature and pressure control and a stirrer. A predetermined quantity of catalyst, toluene and solvent were charged in the reactor at room temperature. The reactor was boxed up and flushed twice with nitrogen. It was then pressurized with 5% $O_2$ (balance $N_2$) up to required pressure and was heated to a desired temperature under minimum stirring. After attaining the desired temperature the stirrer speed was increased to 1000 rpm and the zero time was noted along with the reactor pressure. The reaction was continued for 2 hours. The reactor was then cooled to 15° C., and the gases were analyzed for the content of CO and $CO_2$ by GC. As the reaction is carried out with lean oxygen, it was necessary to pressurize the reactor again with oxygen. The reaction was further continued for two more hours. The reactor was cooled and the contents were analyzed by GC and HPLC and the products confirmed by GCMS.

In a typical experiment, the reactor was charged with toluene 10 g (108 mmole), manganese acetate 0.265 gm, iron chloride 0.178 gm, sodium bromide 0.065 gm and acetic acid 50.0 gm. After flushing with nitrogen, 5% oxygen (balance nitrogen) was introduced to a pressure of 55 bar and the reaction was carried out at 120° C. The results are presented in Table 1.

EXAMPLE 2

This example illustrates the effect of temperature on the conversion and selectivity in the liquid phase oxidation of toluene. The experimental procedure followed as described in Example 1. The reactor was charged with toluene 10.0 gm, manganese acetate 0.265 gm, iron chloride 0.178 gm, sodium bromide 0.065 gm and acetic acid 50.0 gm. After flushing with nitrogen, 5% oxygen (balance nitrogen) was introduced to a pressure of 55 bar and the reaction was carried out at different temperatures. The results are presented in Table 1.

TABLE 1

| Temperature (° C.) | Toluene conversion (%) | Selectivity (%) | | |
| --- | --- | --- | --- | --- |
| | | PhCHO | PhCOOH | $PhCH_2OH$ |
| 100 | 5.9 | 75.4 | 6.9 | 17.8 |
| 120 | 17.1 | 76.8 | 22.0 | 1.2 |
| 140 | 20.1 | 48.5 | 30.6 | 20.5 |

EXAMPLE 3

This example illustrates the effect of pressure on the conversion and selectivity in the liquid phase oxidation of toluene. The reaction was carried out as described in Example 1. The reactor was charged with toluene 10.0 gm, manganese acetate 0.265 gm, iron chloride 0.178 gm, sodium bromide 0.065 gm and acetic acid 50.0 gm. After flushing with nitrogen, 5% oxygen was introduced. The reaction was carried out at 120° C. at 30 and 40 bar pressures. The results are presented in Table 2.

TABLE 2

| Pressure (Bar) | Toluene conversion % | Selectivity % | | |
| --- | --- | --- | --- | --- |
| | | PhCHO | PhCOOH | $PhCH_2OH$ |
| 30 | 10.8 | 78.9 | 12.0 | 9.1 |
| 40 | 12.1 | 72.2 | 13.5 | 14.4 |

EXAMPLE 4

This example illustrates the effect of molar ratio of manganese to iron on the conversion and selectivity in the liquid phase oxidation of toluene. The reaction was carried out as described in Example 1. The reactor was charged with toluene 10.0 gm, manganese acetate 0.265 gm, iron chloride 0.350 gm (Mn/Fe mole ratio=0.5), sodium bromide 0.065 gm and acetic acid 50.0 gm. After flushing with nitrogen, 5% oxygen was introduced to a pressure of 55 bar and the reaction was carried out at 120° C. at various Mn/Fe mole ratios of 0.5 and 2.0. The results are presented in Table 3.

TABLE 3

| Mn/Fe Mole ratio | Toluene conversion % | Selectivity % | | |
| --- | --- | --- | --- | --- |
| | | PhCHO | PhCOOH | $PhCH_2OH$ |
| 0.5 | 9.3 | 70.2 | 13.2 | 16.6 |
| 2.0 | 19.1 | 63.4 | 22.1 | 14.5 |

EXAMPLE 5

This example illustrates the effect of substrate to catalyst ratio on the conversion and selectivity in the liquid phase oxidation of toluene using Mn/Fe/Br catalyst system. The experimental procedure followed as described in Example 1. The reactor was charged with toluene 10.0 gm, manganese acetate 0.53 gm, iron chloride 0.348 gm, sodium bromide 0.112 gm and acetic acid 50.0 gm. After flushing with nitrogen, 5% oxygen was introduced to a pressure of 55 bar and the reaction was carried out at 120° C. at various substrates to catalyst (Mn or Fe) mole ratios. Mn or iron to Br mole ratio is 2.0. Results are presented in Table 4.

TABLE 4

| Substrate/catalyst mole ratio | Toluene conversion % | Selectivity (%) | | |
| --- | --- | --- | --- | --- |
| | | PhCHO | PhCOOH | $PhCH_2OH$ |
| 50 | 19.1 | 63.4 | 22.1 | 14.5 |
| 200 | 2.1 | 67.2 | 14.8 | 18.6 |

EXAMPLE 6

This example illustrates the effect of temperature on the conversion and selectivity in the liquid phase oxidation of toluene using Mn/V/Br catalyst system. The experimental procedure followed as described in Example 1. The reactor was charged with toluene 10.0 gm, manganese acetate 0.265 gm, ammonium metavanadate 0.127 gm, sodium bromide 0.065 gm and acetic acid 50.0 gm. After flushing with nitrogen, 5% oxygen was introduced to a pressure of 55 bar and the reaction was carried out at various temperatures. The results are presented in Table 5.

TABLE 5

| Temperature (° C.) | Toluene conversion (%) | Selectivity (%) | | |
|---|---|---|---|---|
| | | PhCHO | PhCOOH | PhCH$_2$OH |
| 100 | 6.8 | 72.9 | 4.1 | 23.1 |
| 120 | 23.0 | 63.4 | 7.8 | 28.8 |
| 140 | 31.8 | 41.0 | 4.9 | 54.1 |

EXAMPLE 7

This example illustrates effect of pressure on conversion and selectivity in the liquid phase oxidation of toluene using Mn/V/Br catalyst system. The reaction was carried out as described in Example 1. Reactor was charged with toluene 10 g (108 mmole), manganese acetate 0.265 gm, ammonium metavanadate 0.127 gm, sodium bromide 0.065 gm and acetic acid 50.0 gm. After flushing with nitrogen, 5% oxygen was introduced and reactions were carried out at 120° C. at 30 and 40 bar pressures. Results are presented in Table 6.

TABLE 6

| Pressure (Bar) | Toluene conversion % | Selectivity % | | |
|---|---|---|---|---|
| | | PhCHO | PhCOOH | PhCH$_2$OH |
| 30 | 11.2 | 70.0 | 5.7 | 24.3 |
| 40 | 13.5 | 62.7 | 2.9 | 34.5 |

EXAMPLE 8

This example illustrates the effect of molar ratio of manganese to vanadium on the conversion and selectivity in the liquid phase oxidation of toluene. The reaction was carried out as described in Example 1. The reactor was charged with toluene 10.0 gm, manganese acetate 0.137 gm, ammonium metavanadate 0.131 gm (Mn/V mole ratio=0.5), sodium bromide 0.065 gm and acetic acid 50.0 gm. After flushing with nitrogen, 5% oxygen was introduced to a pressure of 55 bar and the reactions were carried out at 120° C. and various Mn/V mole ratios of 0.5 and 2.0. The reaction was also carried out without addition of manganese. The results are presented in Table 7.

TABLE 7

| Mn/V mole Ratio | Toluene conversion % | Selectivity % | | |
|---|---|---|---|---|
| | | PhCHO | PhCOOH | PhCH$_2$OH |
| 0.5 | 16.0 | 76.0 | 9.0 | 15.2 |
| 2.0 | 19.4 | 62.4 | 7.9 | 29.7 |

EXAMPLE 9

This example illustrates effect of substrate to catalyst ratio on conversion and selectivity in liquid phase oxidation of toluene using Mn/V/Br catalyst system. The reaction was carried out as described in Example 1. Reactor was charged with toluene 10 g (108 mmole), manganese acetate 0.530 gm, ammonium metavanadate 0.253 gm, sodium bromide 0.121 gm and acetic acid 50.0 g. After flushing with nitrogen, 5% oxygen was introduced to a pressure of 55 bar and the reaction was carried out at 120° C. at various substrates to catalyst (Mn or V) mole ratios. Mn to Br molar ratio is 2.0. Results are presented in Table 8.

TABLE 8

| Substrate/catalyst mole ratio | Toluene conversion % | Selectivity (%) | | |
|---|---|---|---|---|
| | | PhCHO | PhCOOH | PhCH$_2$OH |
| 50 | 32.4 | 44.0 | 28.4 | 27.7 |
| 200 | 14.0 | 34.9 | 4.1 | 61.0 |

EXAMPLE 10

This example illustrates the effect of the presence or absence of bromine on the conversion and selectivity in the liquid phase oxidation of toluene using Mn/V/Br catalyst system. The experimental procedure followed as described in Example 1. The reactor was charged with toluene 10.0 gm, manganese acetate 0.263 gm, ammonium metavanadate 0.253 gm (Mn/V mole ratio=0.5), sodium bromide 0.121 gm and acetic acid 50.0 gm. After flushing with nitrogen, 5% oxygen was introduced to a pressure of 55 bar and the reactions were carried out at 120° C. and various Mn/V mole ratios and concentration of bromine. The reaction was also carried out in absence of bromine promoter. No activity was observed in absence of bromide promoter and hence it can be concluded that the bromine promoter is essential for the reaction to proceed. The results are presented in Table 9.

TABLE 9

| Mn/V mole ratio | Bromine Conc.* (mol %) | Toluene conversion (%) | Selectivity (%) | | |
|---|---|---|---|---|---|
| | | | PhCHO | PhCOOH | PhCH$_2$OH |
| 1.0 | 0 | No activity | | | |
| 0.5 | 1.09 | 24.7 | 68.7 | 11.3 | 20.0 |

*Bromine concentration with respect to toluene

EXAMPLE 11

The experiment was carried out without the addition of manganese to check its effect on the conversion and selectivity in the liquid phase oxidation of toluene with following the procedure given in Example 1. The reactor was charged with toluene 10.0 gm, ammonium metavanadate 0.131 gm, sodium bromide 0.065 gm and acetic acid 50.0 gm. After flushing with nitrogen, 5% oxygen was introduced to a pressure of 55 bar and the reaction was carried out at 120° C. In this experiment, only 2.7% conversion of toluene and 72.3% and 27.7% selectivity were obtained for benzaldehyde and benzyl alcohol, respectively.

EXAMPLE 12

The experiment was carried out without the addition of vanadium to check its effect on the conversion and selectivity in the liquid phase oxidation of toluene with following the procedure given in Example 1. The reactor was charged with toluene 10.0 gm, manganese acetate 0.262 gm, sodium bromide 0.065 gm and acetic acid 50.0 gm. After flushing with nitrogen, 5% oxygen was introduced to a pressure of 55 bar and the reaction was carried out at 120° C. In this experiment, 10.2% toluene conversion and 61.4%, 16.4% and 22%, selectivity was obtained for benzaldehyde, benzoic acid and benzyl alcohol, respectively.

THE ADVANTAGES OF THE PRESENT INVENTION ARE

1. The present invention produces benzaldehyde as a major product with high selectivity (preferably 60–75%) at higher conversion of toluene.
2. The present invention eliminates the effluent problem, which is the major drawback of the conventional processes due to the use of hydrochloric acid. Moreover, the present invention produces low amount of benzoic acid compared to conventional processes.
3. The catalyst system reported in the present invention works at a lower temperature and hence the formation of carbon dioxide is negligible which ultimately affect the yield and loss of solvent acetic acid, thus the process is environmentally benign.

We claim:
1. A process for the preparation of benzaldehyde comprising:
   (i) subjecting toluene to liquid phase oxidation in a reaction mixture comprising:
      (a) an organic solvent;
      (b) a catalyst system comprising at least one transition metal and a bromide promoter; and
      (c) diluted oxygen, wherein the concentration of oxygen is in the range of from 1 to 10% in nitrogen before the reaction commences,
   (ii) cooling the reaction mixture to room temperature and
   (iii) separating the benzaldehyde.
2. The process as claimed in claim 1 wherein the benzaldehyde is separated by distillation.
3. process as claimed in claim 1 wherein thetransitional metal is selected from the group consisting of manganese, chromium, iron, vanadium,molybdenum, and a combination thereof.
4. The process as claimed in claim 3 wherein the transition metal catalyst comprises a combination of manganese and iron.
5. The process as claimed in claim 4 wherein the mole ratio of manganese to iron is in the range from 0.1 to 10.
6. The process as claimed in claim 5 wherein the mole ratio of manganese to iron is in the range from 0.2 to 5.0.
7. The process as claimed in claim 1 wherein the transitional metal is a salt selected from the group consisting of acetates, bromides, carbonates, fluoride, iodides, chlorides, nitrates, sulfates and vanadates.
8. The process as claimed in claim 7 wherein the transitional metal is a salt selected from the group consisting of acetates, chlorides and vanadates.
9. The process as claimed in claim 1 wherein the bromide promoter is selected from the group consisting of sodium bromide, hydrogen bromide and zinc bromide.
10. The process as claimed in claim 1 wherein the bromide promoter comprises sodium bromide.
11. The process as claimed in claim 3 wherein the concentration of manganese with respect to toluene is in the range of 0.1–7 mol %.
12. The process as claimed in claim 3 wherein the concentration of manganese with respect to toluene is in the range of 0.3–5.0 mol %.
13. The process as claimed in claim 3 wherein the concentration of iron with respect to toluene is in the range of 0.1–5 mol %.
14. The process as claimed in claim 3 wherein the concentration of iron with respect to toluene is in the range of 0.3–4.0 mol %.
15. The process as claimed in claim 3 wherein the concentration of bromine with respect to toluene is in the range of 0.05–5.0 mol %.
16. The process as claimed in claim 3 wherein the concentration of bromine with respect to toluene is in the range of 0.1–3.0 mol %.
17. The process as claimed in claim 1 wherein the organic solvent is selected from the group consisting of an aliphatic acid and an aromatic organic acid, or a combination thereof.
18. The process as claimed in claim 1 wherein the organic solvent is selected from the group consisting of acetic acid, benzoic acid and propionic acid.
19. The process as claimed in claim 1 wherein the organic solvent comprises acetic acid.

20. The process as claimed in claim 1 wherein the concentration of oxygen is in the range of 2–7% in nitrogen.

21. The process as claimed in claim 1 wherein the reaction is carried out at a temperature in the range of 70°–180° C. and pressure in the range of 1–80 bar.

22. The process as claimed in claim 1 wherein the reaction is carried out at a temperature in the range of 90°–160° C. and pressure in the range of 20–70 bar.

23. The process as claimed in claim 1 wherein the selectivity to benzaldehyde obtained is in the range of 60–75% and benzoic acid and benzyl alcohol are obtained as side products.

24. The process as claimed in claim 3 wherein the transition metal catalyst comprises a combination of manganese and vanadium.

25. The process as claimed in claim 24 wherein the mole ratio of manganese to vanadium is in the range from 0.1 to 10.

26. The process as claimed in claim 25 wherein the mole ratio of manganese to vanadium is in the range from 0.2 to 5.0.

27. The process as claimed in claim 3 wherein the concentration of vanadium with respect to toluene is in the range of 0.1–5 mol %.

28. The process as claimed in claim 3 wherein the concentration vanadium with respect to toluene is in the range of 0.3–4.0 mol %.

* * * * *